United States Patent [19]

Miller et al.

[11] Patent Number: 5,189,831

[45] Date of Patent: * Mar. 2, 1993

[54] METHOD AND DEVICE FOR THE BIOLOGICAL CONTROL OF FLYING INSECTS

[75] Inventors: David W. Miller, Amherst, Mass.; Fernando Agudelo-Silva, San Francisco, Calif.; Haim B. Gunner, Amherst; Vanessa F. LeFevre, Northampton, both of Mass.; Meir Broza, Haifa, Israel

[73] Assignee: EcoScience Corporation, Worcester, Mass.

[ * ] Notice: The portion of the term of this patent subsequent to Oct. 15, 2008 has been disclaimed.

[21] Appl. No.: 572,486

[22] Filed: Aug. 23, 1990

Related U.S. Application Data

[63] Continuation-in-part of Ser. No. 324,461, Mar. 15, 1989, Pat. No. 5,057,315.

[51] Int. Cl.⁵ .................. A01N 63/04; A01M 1/10
[52] U.S. Cl. .................. 43/121; 424/93 Q; 424/405; 424/195.1; 43/132.1
[58] Field of Search .......... 43/132.1, 121; 424/405, 424/93, 93 Q, 195.1

[56] References Cited

U.S. PATENT DOCUMENTS

| Re. 29,358 | 8/1977 | Tomcufcik | 542/417 |
|---|---|---|---|
| D. 269,290 | 6/1983 | Carlsen | D22/19 |
| D. 275,124 | 8/1984 | Carlsen | D22/19 |
| D. 278,842 | 5/1985 | Woodruff | D22/19 |
| 3,337,395 | 8/1967 | Page | 424/405 |
| 3,851,417 | 12/1974 | Wunsche | 43/121 |
| 3,908,302 | 9/1975 | Carr | 43/107 |
| 3,913,259 | 10/1975 | Nishimura et al. | 43/114 |
| 3,931,692 | 1/1976 | Hermanson | 424/84 |
| 3,940,874 | 3/1976 | Katsuda | 43/114 |
| 4,030,233 | 6/1977 | Wunsche | 43/121 |
| 4,152,862 | 5/1979 | Mohiuddin | 43/121 |
| 4,173,093 | 11/1979 | Nakai | 43/121 |
| 4,208,828 | 6/1980 | Hall et al. | 43/114 |
| 4,316,344 | 2/1982 | Carlsen | 43/114 |
| 4,395,842 | 8/1983 | Margulies | 43/114 |
| 4,400,905 | 8/1983 | Brown | 43/132.1 |

(List continued on next page.)

OTHER PUBLICATIONS

Archbold, et al., *Environ. Entomol.* 15(1), 221–226 (1986).
Strand and Brooks, *Pathogens of medically important arthropods* Roberts & Strand, editors *Bulletin of the World Health Organization* 55 (Supp. No. 1) pp. 289–304 (Boyce Thompson Inst., Yonkers, N.Y. 10701)*.
Ryan and Nicholas, *J. Inveterbrate Path.* 19, 299–307 (1972).
Appel, et al., *Comp. Biochem. Physiol. A. Comp. Physiol.* 88(3) 491–494 (1987).
Verrett, et al., *J. Econ. Entomol.* 80(6), 1205–1212 (1987).
Archbold, et al., *J. Med. Entomol.* 24(2), 269–272 (1987).
Gunnarsson, S. G. S., *J. Invertebr. Pathol.* (46)3, 312–319 (1985).
Lin, et al., *Natural Enemies of Insects* 9(3), 168–172 (1987)*.

*Primary Examiner*—Ronald W. Griffin
*Assistant Examiner*—Ralph Gitomer
*Attorney, Agent, or Firm*—Kilpatrick & Cody

[57] ABSTRACT

A method for control and extermination of flying insects, especially the housefly, by infection of the insects with an entomopathogenic fungus, preferably soil-dwelling fungi, by means of an infection chamber. The chamber maintains the spores of a fungus pathogenic to the insects in a viable form, serves as an attractant for the insects, and serves to inoculate the insects with high numbers of spores. The spores attach to the insects and originate germ tubes that penetrate into the insect, resulting in death within three to four days. The chamber design, i.e., shape and color, can be the sole attractants for the insects. Alternatively, food or scents can be used to further enhance the attraction of the insects for the chamber. Although the primary means of infection is by external contact with the fungal growth, the insects may also be infected by contact with each other and by ingestion of the spores.

13 Claims, 5 Drawing Sheets

U.S. PATENT DOCUMENTS

| | | | |
|---|---|---|---|
| 4,411,094 | 10/1983 | Spackova et al. | 43/121 |
| 4,423,564 | 1/1984 | Davies et al. | 43/121 |
| 4,563,836 | 1/1986 | Woodruff et al. | 43/131 |
| 4,608,774 | 9/1986 | Sherman | 43/114 |
| 4,642,935 | 2/1987 | Fierer | 43/121 |
| 4,696,127 | 9/1987 | Dobbs | 43/121 |
| 4,709,502 | 12/1987 | Bierman | 43/112 |
| 4,894,947 | 1/1990 | Brandli | 43/131 |
| 4,908,315 | 3/1990 | Kertz | 435/299 |
| 4,921,703 | 5/1990 | Higuchi | 424/419 |
| 5,057,316 | 10/1991 | Gunner | 424/93 |

METHOD AND DEVICE FOR THE BIOLOGICAL CONTROL OF FLYING INSECTS

This is a continuation-in-part of U.S. Ser. No. 7/324,461 entitled "Method and Device for the Biological Control of Cockroaches" filed Mar. 15, 1989, by Haim B. Gunner, Fernando Agudelo-Silva, and Carol A. Johnson issued Oct. 15, 1991 as U.S. Pat. No. 5,057,315.

BACKGROUND OF THE INVENTION

The present invention is in the field of biological control of insect pests, specifically in the area of use of entomopathogenic fungi for the control of flying insects.

Control of the house fly is of major economic importance throughout the world because of public health concerns. The fly has the potential to mechanically transmit a wide variety of human pathogens, as reviewed by Bida Wid, S. P., J. I. Braim and R. M. Matossian, *Ann. Trop. Med. Parasitol.* 72(2): 117-121 (1978). The fly can also be annoying to people, livestock and poultry, to the extent that it even decreases time spent by animals in feeding, thereby decreasing feed efficiency.

Because of the economic and public health importance of the house fly, a significant amount of effort has been devoted to develop methods to control it. The biggest effort has been directed towards chemical insecticides, as reviewed by J. G. Scott and D. A. Rutz, *J. Econ. Entomol.* 81(3): 804-807 (1988). The use of chemical insecticides has a number of serious drawbacks, such as the destruction of non-target biological control agents, development of insecticide resistance, harmful levels of insecticide residue and environmental pollution. Therefore, it is desirable to have less ecologically-disruptive means to control house flies.

New approaches to fly control include the use of parasitoid wasps of various genera, as reported by J.D. Mandeville, et al. *Can Ent* 120: 153-159 (1988). This method of control reduces the fly population but is not adequate in itself to provide satisfactory fly control.

Insect pathogens are a possible alternative to the common use of highly toxic chemical insecticides for the control of insect pests. Fungi are one of the promising groups of insect pathogens suitable for use as biological agents for the control of insects.

Fungi are found either as single cell organisms or as multicellular colonies. While fungi are eukaryotic and therefore more highly differentiated than bacteria, they are less differentiated than higher plants. Fungi are incapable of utilizing light as an energy source and therefore restricted to a saprophytic or parasitic existence.

The most common mode of growth and reproduction for fungi is vegetative or asexual reproduction which involves sporulation followed by germination of the spores. Asexual spores, or conidia, form at the tips and along the sides of hyphae, the branching filamentous structures of multicellular colonies. In the proper environment, the conidia germinate, become enlarged and produce germ tubes. The germ tubes develop, in time, into hyphae which in turn form colonies.

One would expect that pathogens had been extensively considered as biological control agents, however, a review of the literature reveals the scarcity of pathogens that appear to offer potential to control *M. domestica*. The bulk of scientific literature on associations of pathogens with house flies refers to isolated reports of diagnosis of dead flies or laboratory studies without practical, short-term applications.

An extensive review of the literature reveals only isolated cases of fungal infection (see, for example, Table 1 in Briggs and Milligan, *Bull. World Health Organization* 58(Supplement): 245-257 (1980); Briggs and Milligan, *Bull. World Health Organization* 55(Supplement): 129-131 (1977)). Most reports of fungi associated with flies appear to refer to situations where the fungi did not cause patent infections or major predictable collapses of fly populations. Therefore, it does not appear as though fungi can be practically used for fly control. For example, although the fungi *Aspergillus niger, A. flavus, A. ustus* and *Mucor racemosus* from pupae or adults of *M. domestica* by Zuberi, et al., *Pakistan J. Sci. Ind. Res.* 12, 77-82 (1969) there was no evidence that these fungi were inflicting serious pathological effect on the fly populations.

It is possible to infect adult house flies with fungi under certain laboratory conditions, leading to death of the infected flies. For example, *Aspergillus flavus* was pathogenic to *M. domestica* when the insects were fed high concentrations (up to $1 \times 10^9$) of fungal spores, presumably due to toxins in the spores. Mortality after seven days of exposure was 57%; mortality was 100% twenty-one days after exposure. One hundred percent mortality occurred in flies seven days after they were anesthetized and placed in contact with fungal spores, as reported by Amonker and Nair, *J. Invertebr. Pathol.* 7: 513-514 (1965). Dresner, *J. N.Y. Entomol. Soc.* 58: 269-279 (1950), also reported that an isolate of the fungus *Beauveria bassiana* infected adult *M. domestica* when the insects were exposed to a dust of germinating conidia adhered in a nutrient medium. The fungus was also infective to flies when the insects were exposed to a dish of milk containing fungal conidia.

D. C. Rizzo conducted studies, reported in *J. Invert. Pathol.* 30, 127-130 (1977), on the mortality of flies infected with either *Metarhizium anisopliae* or *Beauveria bassiana* and determined that the time to death after infection was independent of age. Flies were infected by rolling them for ten minutes in four-week-old fungal culture slants until they were completely exposed to the spores, then maintaining them in humidity chambers. As noted by the author, in reference to the infecting fungi, "these pathogens have never been reported as having caused mycoses in fly populations in nature" at page 127.

In 1990, however, D. C. Steinkraus, et al., reported in *J. Med. Entomology* 27(3), 309-312, that *Musca domestica L.*, infected with *Beauveria bassiana* had been found on dairy farms in New York, although at a prevalence of less than 1% (28 out of 31,165). Isolates of the fungi were infective for laboratory raised flies, but the low naturally occurring incidence led to the conclusion by the authors that "it seems unlikely that these infections represent naturally occurring epizootics within house fly populations" at page 310.

These studies have led to the recognition that there is a potential for fungal control of insects. However, no one has yet developed a consistent and commercially viable way of infecting insects and assuring that the fungi are dispersed throughout the breeding populations. For example, with reference to house flies, it is clearly impractical, and will make the registration of any product with the Environmental Protection Agency in the United States very difficult, to disperse conidia on surfaces or dishes of nutrient media whenever there is a need to control the fly population.

As of this time, there has been no successful demonstration by others of the practical, reliable and economical employment of an entomopathogenic fungus for the management and biological control of flying insects such as the common housefly.

It is therefore an object of the present invention to biologically control flying insects, especially the housefly, using entomopathogenic fungi.

It is a further object of the present invention to provide a device for the convenient, reliable and economically feasible application of fungi in the biological control of flying insects.

SUMMARY OF THE INVENTION

A method for control and extermination of flying insects, especially the housefly, by infection of the insects with an entomopathogenic fungus by means of an infection chamber. The chamber maintains the spores of a fungus pathogenic to the insects in a viable form, protecting the fungi from the environment (including rain, ultraviolet light and the wind), serves as an attractant for the insects, and serves to inoculate the insects with high numbers of spores. The fungal culture provides a continuous supply of spores over a prolonged period of time, even if desiccated. The spores attach to the insects and originate germ tubes that penetrate into the insect, which can result in death within three to four days. The chamber design, i.e., shape and color, can be the sole attractants for the insects. Alternatively, food or scents can be used to further enhance the attraction of the insects for the chamber. Although the primary means of infection is by external contact, the insects may also be infected by contact with each other and by ingestion of the spores.

The two most preferred entomopathogenic fungi are *Metarhizium anisopliae* and *Beauveria bassiana*, although other fungi can be used which are pathogenic when the insect is inoculated via the infection chamber, such as Paecilomyces and Verticillium. Examples demonstrate control of *Fannia canicularis* and *Musca domestica* under laboratory conditions and of *Musca domestica* in chicken coops using chambers containing *Metarhizium anisopliae*. Although exemplified as a method for fly control, the chamber can also be used for control of other flying insects that will enter the chamber and be infected by the fungus.

BRIEF DESCRIPTION OF THE DRAWINGS

FIG. 1 is a perspective view of an infection chamber for infection of flies by entomopathogenic fungi, consisting of a housing, culture medium, sporulating fungal culture, and attractant.

DETAILED DESCRIPTION OF THE INVENTION

Under normal circumstances, flying insects are not exposed to high concentrations of spores of soil-dwelling entomopathogenic fungi. The primary advantages of the infection chamber are that (1) it concentrates an extremely high number of fungal inoculum in a very small space within the infection chamber, forcing entering insects into contact with the spores which infect and kill the insects, and (2) it contains the fungal spores, resulting in minimal exposure of the environment to the pathogenic fungi, and protecting the fungus from the environment, thereby increasing viability of the culture and minimizing contamination of the fungal culture.

The devices described below provide a convenient, non-toxic and reliable method for the administration of entomopathogenic fungi in an economical and cost-effective fashion. The small, lightweight infection chambers are unobtrusive and are easily placed in locations of heavy insect infestation, increasing the efficacy of the device. Because the devices provide an environment within which the fungus can flourish over extended periods of time, a single device is effective for a longer period of time than with other methods, such as spraying, where effectiveness of the agent dissipates over a short time. The longevity of the devices also decreases the number of applications and maintenance time required for effective treatment. Another advantage of the devices is that they are constructed of readily available and relatively inexpensive materials, which insures an abundant supply of cost-effective devices.

Although described with reference to flies, especially the common housefly *M. domestica*, the term "flies" is used to refer to any type of flying insect which will enter the device and be infected by the entomopathogenic fungi. Examples of flying insects include other flies such as the little housefly (*Fannia canicularis*), tsetse fly, Mediterranean fruit fly, and Oriental fruit fly, wasps, white flies, and the adult forms of some insects, such as the corn rootworm, *Diabrotica undecempunctata*.

In a preferred embodiment, the flies are infected by exposure to the fungus in small chambers having apertures through which the flies enter and exit. A fly enters the chamber either as the result of general exploration or, more generally, as the result of being lured inside the device by the action of fly attractants (such as food sources, pheremones, or the color and shape of the chamber). Once inside the chamber the fly comes in contact with the entomopathogenic fungus. The conidia of the pathogen attach to the body of the fly. The infected fly leaves the chamber. Conidia attached to the fly's integument can be dislodged and may contaminate the habitat, thereby exposing additional flies to infectious spores. Further, after the fly dies and the fungal mycelium sporulates on the body of the insect, other flies can be infected by exposure to the conidia produced on the dead insect.

Figure 1A:
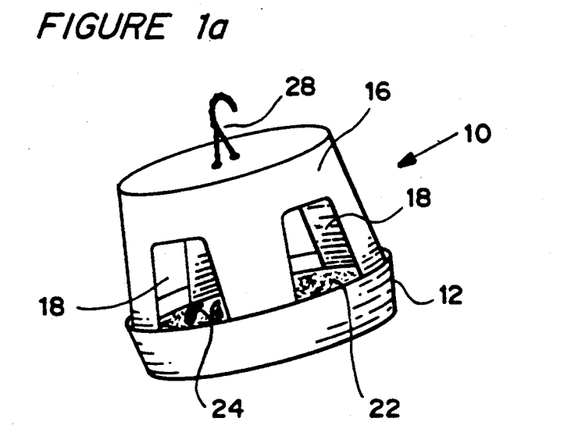
FIG. 1A is viewed from the exterior of the chamber.
Figure 1B:
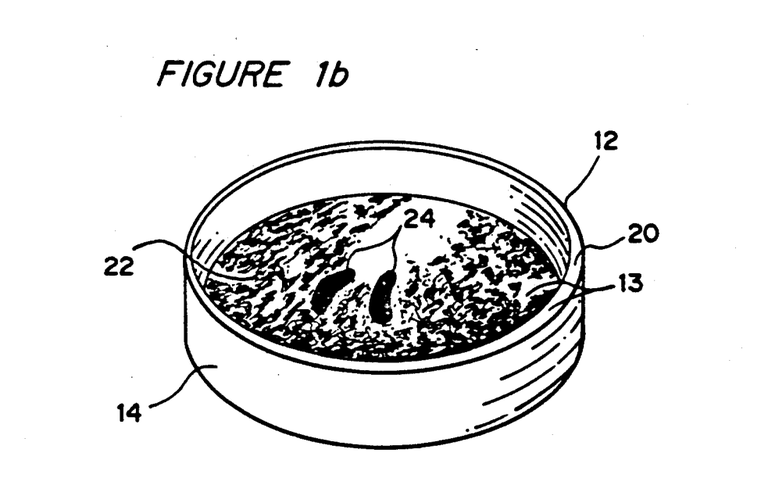
FIG. 1B is a view of the interior bottom portion of the chamber.
Figure 2:
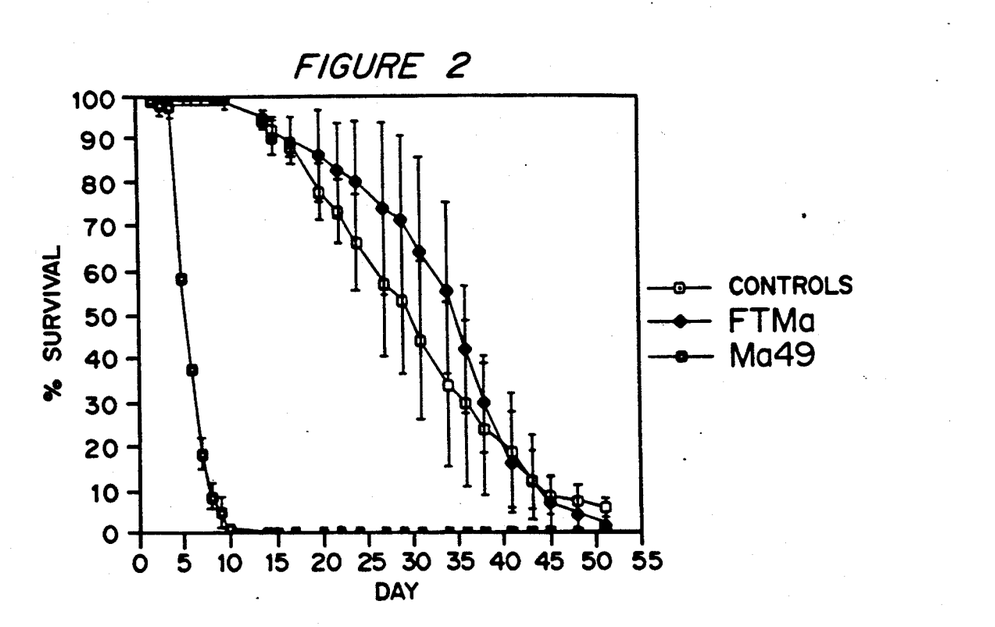
FIG. 2 is a graph of the mortality of *M. domestica* (% survival) as a function of time after exposure (days) to a chamber containing *Metarhizium anisopliae* (-[]-); formaldehyde treated fungus (diamond); or chamber without fungus (-[-]-).
Figure 3:
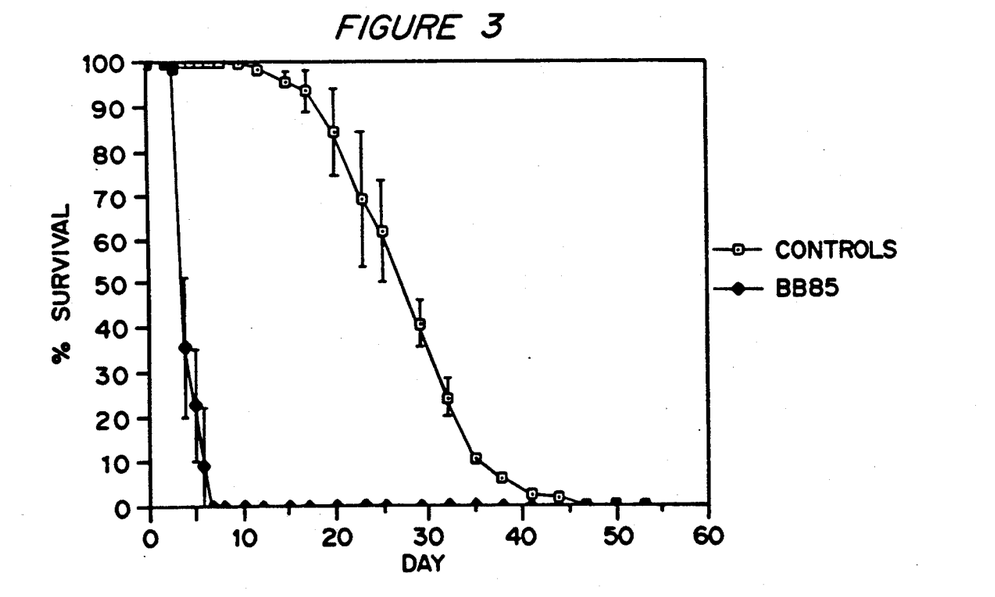
FIG. 3 is a graph of the mortality of *M. domestica* (% survival) as a function of time after exposure (days) to a chamber containing *Beauveria bassiana* (diamond) or chamber without fungus (-[-]-).

As diagrammed in FIG. 1, an infection chamber 10 can be constructed using standard technology to form a container 12 for fungal culture medium 14 and a cover 16 for the chamber, having openings 18 allowing insects free access to the interior of the chamber. The fungus grows on the medium 14, forming mycelia 20 and spores 22. A food attractant 24 is located on the interior of the chamber 10, in close proximity to the spores 22. The attractant is optionally located on a platform secured to the container 12 or the cover 16 to avoid direct contact with the fungus, which can serve as a landing platform for the flies. The moisture content can be regulated by the design of the chamber, for example, by the size and number of openings. In the preferred embodiment, the chamber is hung via a hook 28 in a location most likely to attract flying insects.

The chamber can be constructed using conventional materials, including glass or metal, but is preferably constructed of an extrudable or moldable plastic to keep costs to a minimum. The chamber must have openings large enough to allow free passage of the insects. The top of the chamber preferably fits securely over the bottom, or the chamber is constructed of one piece. The location of food attractants and landing platform, if any, should be such that the insects are forced into close contact with the spores. The chamber can be designed so that the fungus grows on the bottom, top and/or sides of the chamber, to maximize infectivity. The insects are infected when they contact the fungus in the chamber, or when during grooming from spores acquired on their feet.

Suitable culture media are known which can be used in the chamber. Examples of media known to those skilled in the art and which are commercially available include potato, dextrose, agar, or rice agar.

An example of a useful culture medium for Metarhizium and Beauveria consists of 1% dextrose, 1% yeast extract, 5% rice flour, 1.5% agar and 0.5% 5× Dubois sporulation salts. The 5× Dubois sporulation salts consists of 15 g $(NH_4)_2SO_4$ /1000 ml; 0.30 g $MgSO_4$ $7H_2O$/1000 ml; 0.15 g MnSO. $H_2O$/1000 ml; 0.0375 g $CuSO_4$ $5H_2O$/1000 ml; 0.0375 g $ZnSO_4$ $7H_2$/1000 ml; and 0.0038 g $FeSO_4$ $7H_2O$/1000 ml. Each salt is completely dissolved before the next salt is added and the solution is autoclaved.

The culture medium is inoculated with spores of the appropriate fungal pathogen (inoculation is accomplished by streaking the surface of the medium with an inoculating loop carrying fungal spores or by mixing the spores with the liquid medium). After seven days of growth at 28° C. with 75% relative humidity, the fungus will have produced a thick layer of mycelia and conidia that cover the surface of the culture medium.

Attractants that are useful will be dependent on the type of flying insect to be controlled. For example, attractants for flies include fruit, such as raisins, pheromones such as the sex pheromone muscalure, described by Carlson and Bereza *Environ. Entomol.* 2, 555-560 (1973), and synthetic compounds, such as the feeding attractant Lursect™, McClaughlin, Gormley and King Co., Minneapolis, Mn. The shape and/or color of the chamber, as well as the location of the chamber, can also be used to attract flying insects. Three studies conducted on the spatial and temporal responses of flies to attractive bait, and the attractiveness and formulation of different baits, are reported by Willson and Mulla, in *Environ. Entomol.* 4(3), 395-399 (1975) and 2(5), 815-822 (1973) for *Musca domestica* and by Mulla, et al., *Environ. Entomol.* 66(5), 1089-1094 (1973).

At least two species of entomopathogenic fungi have been shown to be effective in control of the housefly, *Metarhizium anisopliae* and *Beauveria bassiana.* Others that should be useful are fungi that are easy to grow on artificial media and quickly grow and produce large amounts of conidia. Examples include Verticillium and Paecilomyces spp.

The following non-limiting examples demonstrate the efficacy of the infection chambers in controlling flies. In all cases the fly populations were significantly reduced by the fungus present in the infection chambers.

EXAMPLE 1

Infection of *Musca domestica* with Fungi in Infection Chambers

House fly pupae were placed in closed cages that had either a fly chamber with sporulating fungus (treatment chamber) or a control chamber without fungus. Vials containing sugary water, cotton, and powdered milk were provided in each cage to assure that the adult flies had an energy source and water when they emerged from the pupae.

After the adult flies emerged, mortality was recorded daily and plotted. Selected dead flies from the treatment chamber were surface-sterilized, examined under the microscope and found to be infected, and incubated in wet chambers to ascertain whether the entomopathogenic fungus that was in the treatment cultures would grow from the dead flies.

Exposure of the adult flies to the chambers containing either the fungi *Metarhizium anisopliae* or *Beauveria bassiana* resulted in a significant reduction in survival of adult house flies as compared to flies exposed to chambers without fungus, as shown by FIGS. 2 and 3, respectively. FIG. 2 summarizes the results of the study where flies were exposed to *M. anisopliae.* 80% of the flies were dead after only five days; almost 100% were dead by seven days following exposure to the fungus. Formaldehyde-killed fungus did not result in a greater mortality than controls exposed to the chambers without fungus. FIG. 3 summarizes the results of the study where flies were exposed to *B. bassiana.* Essentially 100% of the flies were dead by four days following exposure to the fungus.

Dead surface-sterilized flies from the treatment chambers where flies were exposed to *B. bassiana* were found to contain fungus inside of the opened bodies. Control flies not exposed to the fungus did not contain fungus. This demonstrates that the fungus infected the flies and invaded the flies internally before they died.

EXAMPLE 2

Infection of *Fannia canicularis* with Fungi in Infection Chambers

Fly pupae were placed in closed cages. One week after emergence either a fly chamber with sporulating fungus (treatment chamber) or a control chamber without fungus were added to the cage. Vials containing sugar, powdered milk, water and cotton were provided in each cage to assure that the adult flies had an energy source and water when they emerged from the pupae. Fungi were obtained from the American Type Culture Collection, 12301 Parklawn Drive, Rockville, Md. 20852, USA, where they are available without restriction.

Figure 4:
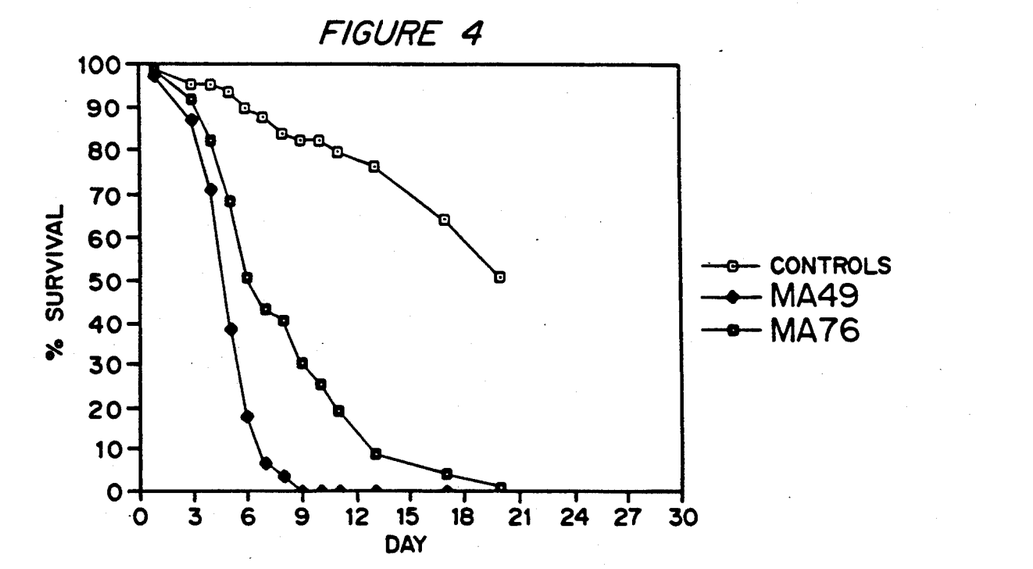
FIG. 4 is a graph of the mortality of *Fannia canicularis* (% survival) as a function of time after exposure (days) to a chamber containing *Metarhizium anisopliae*, strain ATCC MA 38249 (diamond) or ATCC MA 62176 (-[]-), or chamber without fungus (-[-]-).
Figure 5:
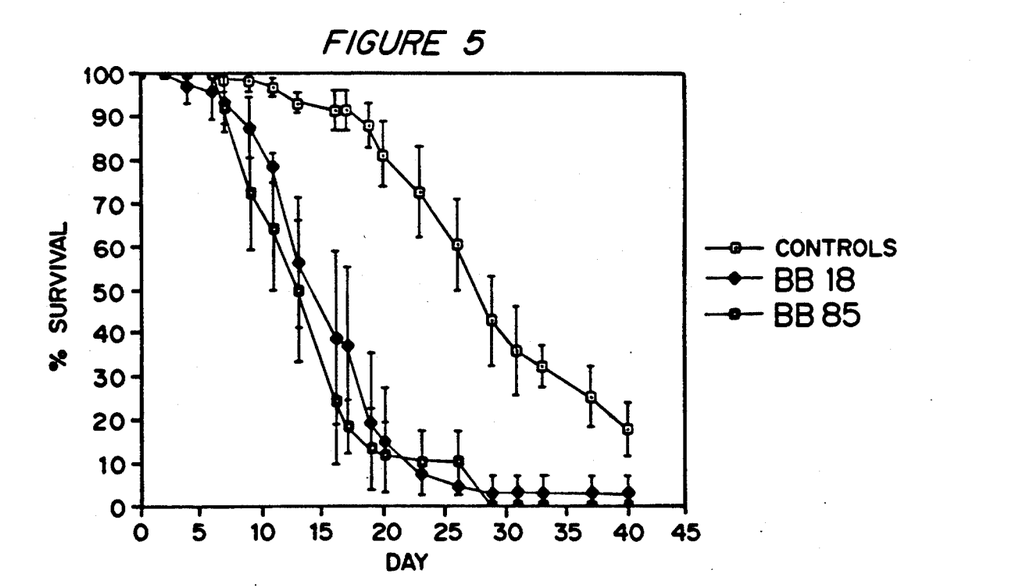
FIG. 5 is a graph of the mortality of *Fannia canicularis* (% survival) as a function of time after exposure (days) to a chamber containing *Beauveria bassiana*, strain ATCC 24318 (diamond) or ATCC 48585 (-[]-), or a chamber without fungus

After the adult flies emerged, mortality was recorded daily and plotted. Exposure of the adult flies to the chambers containing either of two strains of the fungi *Metarhizium anisopliae* or *Beauveria bassiana* resulted in a significant reduction in survival of adult house flies as compared to flies exposed to chambers without fungus, as shown by FIGS. 4 and 5, respectively. FIG. 4 summarizes the results of the study where flies were exposed to *M. anisopliae* strains 62176 and 38249. 80% of the flies were dead after only six days; almost 100% were dead by eight days following exposure to the fungus. FIG. 5 summarizes the results of the study where flies were exposed to *B. bassiana* strains 24318 and 48585. Essentially 100% of the flies were dead by four days following exposure to the fungus.

EXAMPLE 3

Control of *Musca domestica* in chicken coops using chambers containing *Metarhizium anisopliae*

The effectiveness of the chambers containing fungus for control of flies under field conditions, in contrast to laboratory conditions, was determined using two chicken coops 12'×12'×6', containing 20 chambers per coop, fresh chicken and cow manure, and 10,000 *M. domestica* flies. 100 flies were removed per coop four, eight, eleven and fifteen days after exposure to the chambers and reared in the laboratory to determine mortality. Fifteen paper sheets (8.5"×11") were placed in each coop for counting resting flies. Fifteen 3"×5" cards were placed in each coop for counting fecal and vomit spots as an indicator of the number of flies remaining after exposure to the chambers.

Figure 6:
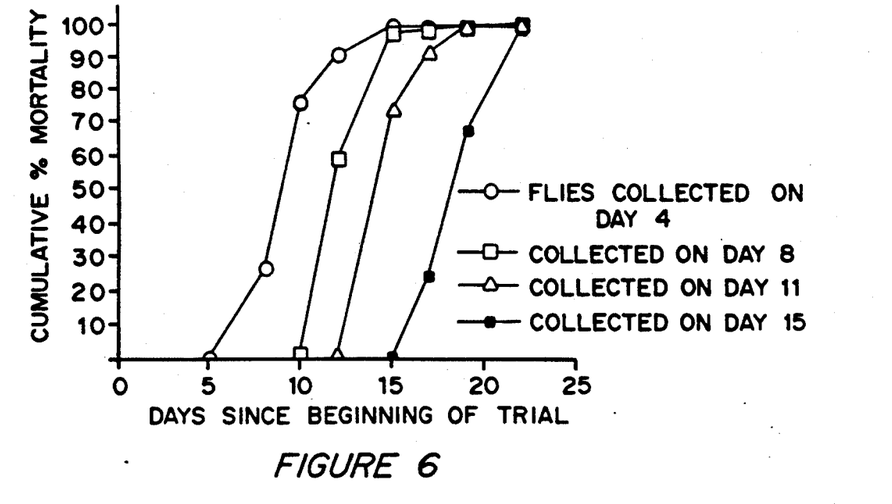
FIG. 6 is a graph of the cumulative percent mortality of *Musca domestica* (10,000 flies/coop) as a function of time after exposure (days) to *Metarhizium anisopliae* in chicken coops: flies collected on day 4 (-0-), flies collected on day 8 (-[]-), flies collected on day 11 (triangle), and flies collected on day 15 (reversed arrows).
Figure 7A:
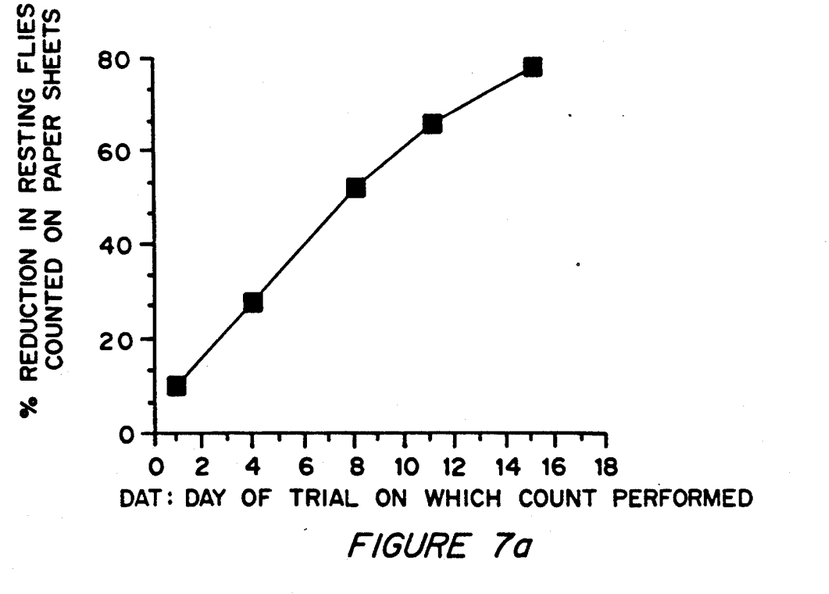
FIG. 7A is the percent reduction in resting flies of *M. domestica* (10,000 flies/coop) as a function after exposure (days) to *M. anisopliae* in chicken coops.
Figure 7B:
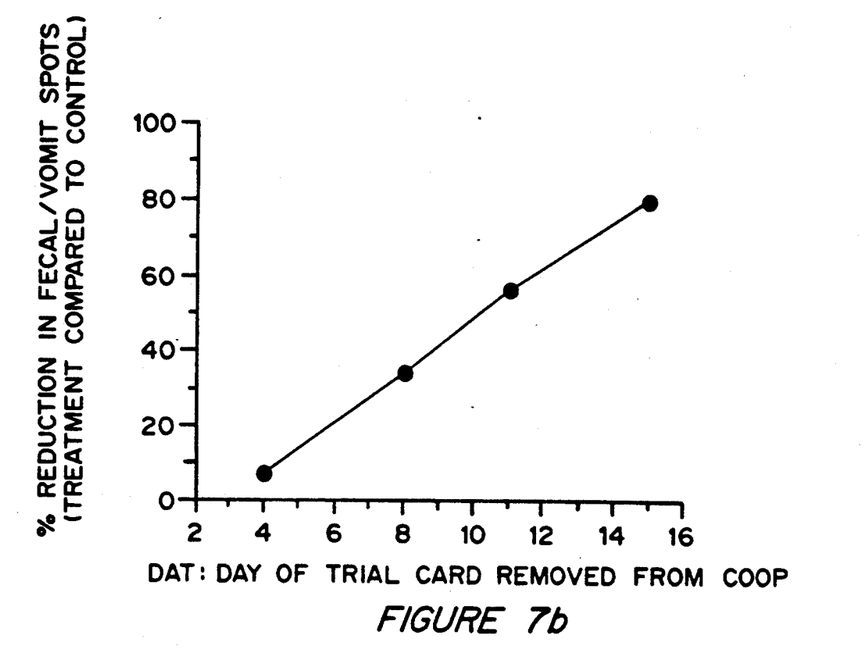
FIG. 7B is the percent reduction in fecal/vomit spots of *M. domestica* (10,000 flies/coop) as a function of time after exposure (days) to *M. anisopliae* in chicken coops.

The results, graphically shown in FIG. 6, demonstrate that 100% mortality was achieved of all flies collected from the coops having chambers containing fungus. The results shown in FIG. 7A of the numbers of resting flies indicate a 78% reduction in flies by the fifteenth day. The results shown in FIG. 7B of the numbers of vomit spots and feces indicate an 80% reduction in flies by the fifteenth day of the study.

Modifications and variations of the method and device for biological control of flying insects using entomopathogenic fungi will be obvious to those skilled in the art from the foregoing detailed description. Such modifications and variations are intended to come within the scope of the appended claims.

We claim:

1. An apparatus for control of flying insects comprising
a chamber attractive for flying insects, having at least one entrance therein for the flying insects, and containing an effective amount to lethally infect the flying insects of a live culture of a fungus that can be pathogenic for the flying insects selected from the group consisting of Metarhizium, Beauveria, Verticillium, Paecilomyces species and combinations thereof, on a nutrient medium, wherein the geometry of the chamber causes the entering insects to contact a lethal amount of the fungus.

2. The apparatus of claim 1 wherein the flying insects are selected from the group consisting of flies, wasps and white flies.

3. The apparatus of claim 1 further comprising means for regulating moisture content of the chamber.

4. The apparatus of claim 1 further comprising a platform within the chamber, in close proximity to the fungal culture.

5. The apparatus of claim 1 wherein the chamber is attractive due to a feature of the chamber selected from the group consisting of color, shape, location, and combinations thereof attractive to the flying insects.

6. The apparatus of claim 1 wherein the chamber is attractive due to a composition selected from the group consisting of chemical attractants and food.

7. A method for increasing the mortality rate of flying insects comprising providing
a chamber attractive for flying insects, having a least one entrance therein for the flying insects, and containing an effective amount to lethally infect the flying insects of a live culture of a fungus that can be pathogenic for the flying insects selected from the group consisting of Metarhizium, Beauveria, Verticillium, Paecilomyces species and combinations thereof on a nutrient medium, wherein the geometry of the chamber causes the entering insects to contact a lethal amount of the fungus.

8. The method of claim 7 wherein the flying insects are selected from the group consisting of flies, wasps and white flies.

9. The method of claim 7 further comprising regulating moisture content of the chamber.

10. The method of claim 7 further providing a platform within the chamber, in close proximity to the fungal culture.

11. The method of claim 7 further comprising making the chamber attractive by making the chamber with a feature selected from the group consisting of color, shape, location, and combinations thereof attractive to the flying insects.

12. The method of claim 7 further comprising making the chamber attractive by adding a composition selected from the group consisting of chemical attractants and food.

13. The method of claim 7 further comprising placing the chamber in a location frequented by the flying insects to be controlled.

* * * * *